United States Patent [19]

Faltynek

[11] Patent Number: 4,474,976

[45] Date of Patent: Oct. 2, 1984

[54] METHOD OF PRODUCING PHENYL SILANES

[75] Inventor: Robert A. Faltynek, Schenectady, N.Y.

[73] Assignee: General Electric Company, Schenectady, N.Y.

[21] Appl. No.: 527,614

[22] Filed: Aug. 29, 1983

[51] Int. Cl.$^3$ .............................................. C07F 7/08
[52] U.S. Cl. .................................................. 556/481
[58] Field of Search ........................................ 556/481

[56] References Cited

U.S. PATENT DOCUMENTS

| | | | |
|---|---|---|---|
| 2,572,302 | 10/1951 | Barry | 260/448.2 |
| 2,598,436 | 5/1952 | Mohler et al. | 556/481 |
| 2,759,960 | 8/1956 | Nishikawa et al. | 556/481 |
| 2,902,504 | 9/1959 | Nitzsche et al. | 556/481 |

OTHER PUBLICATIONS

A. J. Barry, "Direct Process for the Preparation of Arylhalosilanes", Adv. Chem. Series, 23, (1959), 246.
J. O. Hawthorne, "Decarbonylation of Aromatic Aldehydes", J. Org. Chem., 25, (1960), 2215.
J. Blum, "Decarbonylation of Aroyl to Aryl Chlorides", Tetrahedron Letters, No. 15, Pergamon Press, (1966), 1605.
R. N. Haszeldine et al., "Organosilicon Chemistry, Part XII", J.C.S. Dalton, (1974), 2311.
W. A. Gustavson et al., "Formation of Phenylsiloxanes from Benzene and Silicon Hydrides", Organometallics, 1, (1982), 884.
M. F. Semmelhack et al., "Coupling of Aryl Halides with Bis(1,5-cyclooctadiene)nickel(0)", J. Am. Chem. Soc., 93, (1971), 5908.

*Primary Examiner*—Paul F. Shaver
*Attorney, Agent, or Firm*—Richard J. Traverso; James C. Davis, Jr.; James Magee, Jr.

[57] ABSTRACT

A method of producing phenyl silanes is provided by reacting a silane having at least one hydrogen-silicon bond and an aromatic compound having at least one halogen radical, aryl halide radical or aldehyde radical in the presence of a transition metal catalyst at a temperature in the range of about 150° C. to 200° C. Suitable transition metals include rhodium, ruthenium, palladium, osmium, iridium and platinum.

15 Claims, No Drawings

METHOD OF PRODUCING PHENYL SILANES

BACKGROUND OF THE INVENTION

The invention relates to a method of producing aryl silanes. More particularly, this invention relates to a method of effecting reaction between a silane of the formula $$HSiR_3 \quad (I)$$

and a compound of 6 to 30 carbon atoms having an aromatic nucleus (Ar) and at least one monovalent radical selected from the class consisting of halogen (X) and substituted carbonyl groups of the formula

in the presence of an effective amount of transition metal catalyst at a temperature in the range of 150° to 200° C., where R, Ar, Y and X are more particularly defined below.

Aryl silanes are typically utilized as starting materials in the production of aryl-siloxane resins. Prior to this invention aryl silanes were produced by reacting elemental silicon and chlorobenzene at a temperature of about 400° C. in the presence of an effective amount of copper or silver catalyst. The process is disadvantageous in that a significant amount of polychlorinated biphenyls (PCBs) are coproduced. In addition, the high temperature necessary to facilitate reaction requires the use of complex equipment that operates under pressure. The high reaction temperature also places a high energy demand on obtaining the desired product.

An alternative method of producing aryl silanes without producing PCBs is disclosed by Barry in U.S. Pat. No. 2,572,302 and in Advances in Chem. Series 23 (1959) 246. In this process benzene is reacted with chloroorganosilanes in the presence of boron trichloride at about 300° C. Drawbacks in utilizing this process are (1) the expense of maintaining high reaction temperatures and providing the complex equipment necessary to maintain the reactants at such relatively high temperatures and (2) the danger in volatilizing benzene, a highly toxic compound, at temperatures near 300° C.

The present invention overcomes the disadvantage of producing PCBs, does not require the use of temperatures above 200° C. and does not require the use of starting materials, as toxic as benzene.

STATEMENT OF THE INVENTION

As illustrated in formula I, the silanes utilized must have at least 1 hydrogen-silicon bond. The remaining monovalent radicals, R, are selected from a group consisting of hydrogen, halogen and organic radicals of from 1 to 30 carbon atoms. Suitable halogens include chlorine, bromine, fluorine, and iodide. Suitable organic radicals include alkyl radicals of from 1 to 20 carbon atoms, aryl radicals of from 6 to 30 carbon atoms, alkoxy radicals of from 1 to 20 carbon atoms, etc. Particular monovalent alkyl radicals within the scope of R include, for example, methyl, ethyl, propyl, butyl, isopropyl, pentyl, cyclohexyl, etc. Particular monovalent aryl radicals within the scope of R include phenyl, napthyl, tolyl, xylyl, and diaryl groups of the formula:

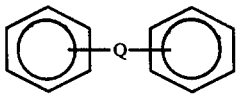

where Q is selected from —O—, —S—,

and alkylene radicals are from 0 to 8 carbon atoms.

Suitable alkoxy radicals include methoxy, ethoxy, propoxy, butoxy, cyclohexoxy, isopropoxy, 2-ethylbutoxy, etc. An example of an acyloxy radical within the scope of R is acetoxy, having the formula

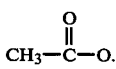

Halogenated derivatives of the above-identified organic radicals, such as 4-chlorophenylene, 2,4-dichlorophenylene, chloromethylene, etc.; and derivatives containing a silicyl radical are within the scope of R and can be utilized without departing from the practice of this invention.

Some examples of silanes which are suitable for use in this invention are, more particularly, dimethylchlorosilane, dipropylsilane, diisopropylsilane, triethylsilane, dipentylsilane, dioctylsilane, dimethyltolyl silane, naphthylsilane, 2,2(4 silicyldiphenyl) propane, 2,2(4,4' disilicyldiphenyl)propane, phenylsilane, trichlorosilane, dichlorosilane, dimethyl propylsilane, dimethylsilane, diethylphenylsilane, dichloro ethylsilane, dichloromethylsilane, dibromomethylsilane, dimethylphenylsilane, etc.

Due to the fact that unsubstituted silane and some monosubstituted halo and alkyl silanes form explosive mixtures with air, they may be undesirable for the production of aryl silanes by this process in conventional equipment. Examples of such silanes include silane, methylsilane, ethylsilane, iodosilane, fluorosilane, isopropyl silane, t-butylsilane. The monosubstituted aryl silanes, such as phenyl silane do not pose the above problems and permit the use of conventional equipment when producing aryl silanes by this process.

The compounds utilized to react with the silanes have an aromatic nucleus, Ar, and at least one monovalent radical selected from the class consisting of halogen (X) and substituted carbonyl groups having the formula:

where Y is selected from a group consisting of halogen and hydrogen. The aromatic compounds which are preferred for use in this invention can be represented by the formulas $$ArX_n \quad (II)$$

and

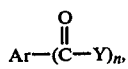 (III)

wherein X and Y are as previously defined and the letter n represents an integer of from 1 to 10 inclusive. Suitable aromatic nuclei (Ar) are selected from a group consisting of polyvalent and monovalent radicals of from 6 to 30 carbon atoms.

Examples of aromatic radicals within the scope of Ar include, for example, phenyl, naphthyl, tolyl, xylyl, aromatic anhydride groups of the formula

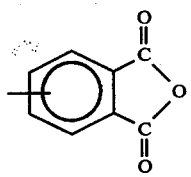

aromatic imides of the formula

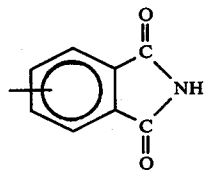

and diaryl groups of the formula

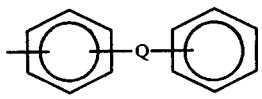

where Q is selected from the group consisting of —O—, —S—,

and alkyl radicals of from 1 to 8 carbon atoms.

Imide and amine derivatives of the above-identified radicals, such as aniline, acetanilide etc.; are also within the scope of Ar and can be utilized without departing from this invention.

The halogens defined by X more particularly include chlorine, bromine, and iodine. Where Y of the formula

is hydrogen, the substituted carbonyl group is an aldehyde group. Where Y of the above formula is halogen, the substituted carbonyl group is an aroyl halide. The halogens within the scope of Y include, chlorine, bromine and iodine and provide the following aroyl halides

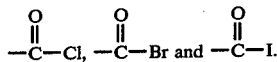

Particular examples of aromatic compounds suitable for use in this invention include the anhydrides: 4-chlorophthalic anhydride and 3-chlorophthalic anhydride; the aromatic imides: 3-phthalimide and 4-chlorophthalimide; the aromatic amines: 2-chlorophenyl amine, 2,5-dichlorophenyl amine, 4,4'-diamino, 3,3'-dichlorodiphenyl and 2,2-(4,4'-diamine 3,3'-dichlorodiphenyl) propane; the acyl halides: benzoyl chloride, benzoyl bromide, phthalyl chloride, terephthaloyl chloride, trimesoyl chloride, pyromellitoyl chloride; the aromatic aldehydes: benzaldehyde, phthalaldehyde, terephthaldehyde; the aryl halides: bromo-benzene, chlorobenzene, 1,4-dichlorobenzene, 1,3,5-trichlorobenzene, 2,6-dimethylchlorobenzene, and 2,4-(4,4'-dichlorodiphenyl)propane; 2-chloro naphthalene, etc.

The transition metals suitable for use as catalysts in the process comprising this invention include, for example, rhodium, ruthenium, palladium, osmium, iridium, and platinum. These transition metals can be utilized as a heterogeneous catalyst within the reaction mixture by combining the metal with an inert substrate, such as carbon or polystyrene. These transition metals may also be utilized as homogeneous catalysts by forming a complex of the transition metal with ligands and dissolving the metal complex in the reaction mixture. It is preferable to utilize low valent species of the above-identified transition metals. For example, rhodium having a valence of 1 is preferred over rhodium species having a valence of 3 or more and platinum having a valence of 0 or 2 is preferred over platinum species having a valence of 4. For palladium, speciees having a valence of 0 and 2 are suitable. For osmium, the preferred valence states are 0 and 2 and for iridium the preferred valence state is 1. Where a homogeneous catalyst of the transition metal is utilized, the transition metal is within a complex of ligands. Any ligand which is capable of donating 1 or 2 electrons is suitable for use in forming a complex with the transition metals utilized in this invention. Suitable ligands include, for example, halides, hydrides, alkyl groups, aryl groups, phosphine groups, carbonyl groups, amines, etc. Examples are transition metal complexes suitable for use in this invention include the following:

Catalyst

ClRh(PPh$_3$)$_3$

ClRh(CO)(PPh$_3$)$_2$

ClRh(CO)(PMe$_3$)$_2$

HRh(CO)(PPh$_3$)$_3$

Cl$_2$Pd(PPh$_3$)$_2$

Me$_2$Pt(PEt$_3$)$_2$

Cl$_2$Ru(PPh$_3$)$_3$

The quantity of catalyst which is preferred falls within the range of about 0.01 to 1.0% by weight of the active ingredients, with a range of about 0.05 to 0.3% by weight being most preferred. The actual metal concentration within the reaction mixture is in the order of about 0.005 to 0.03% of the active ingredients where a complex of the transition metal catalyst is used. Where the transition metal is utilized in a heterogeneous system, the transition metal preferably comprises about 1 to 10% by weight of the solid carrier. The actual metal concentration within the reaction mixture is preferably within the same range defined above for the homogeneous catalyst.

The reaction temperature is preferably within the range of about 150°–200° C. The upper limit of this range is defined by the extent of degradation of transition metal catalyst within the reaction mixture. The lower limit of this reaction temperature range is also defined by the catalyst utilized. The lower limit typically being the minimum temperature at which the catalyst remains active. The most preferred reaction temperature within this range is about 180° C.

The overall reaction is believed to be accomplished in two steps which proceed simultaneously in the same reaction vessel. Where the aromatic compound utilized has a carbonyl group of the formula

the decarbonylation/Si-H addition reactions are believed to proceed as follows, where the aromatic nucleus (Ar) is represented by a phenyl radical

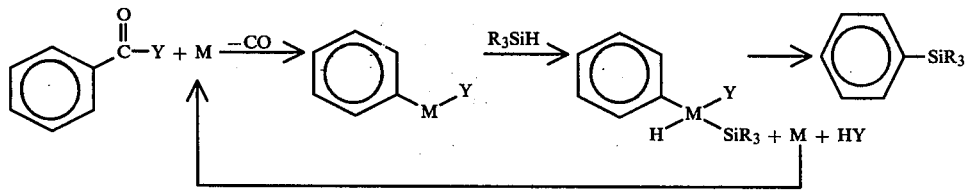

(Y is halogen or hydrogen and M is a transition metal) Where the aromatic compound contains a halogen radical (X) the aryl halide-metal reaction and the Si-H addition is believed to occur in a similar fashion in accordance with the following equation, where the aromatic nucleus (Ar) is represented by a phenyl radical.

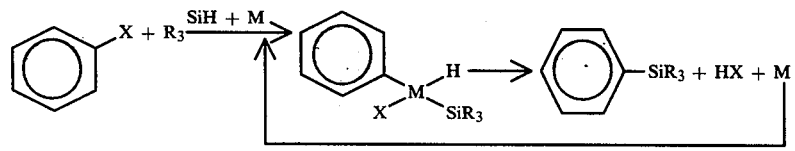

(X is halogen and M is a transition metal)

The reactions above can be carried out with or without a solvent. Non-polar solvents having a boiling point above the reaction temperature utilized are suitable. Those having a boiling point above 200° C., such as dodecane, are preferred.

Both of the reaction mixtures which provide the reactions described above also provide competing side reactions. The following equations describe the principal competing reaction with each mixture, wherein the aromatic nucleus (Ar) is represented by a phenyl radical.

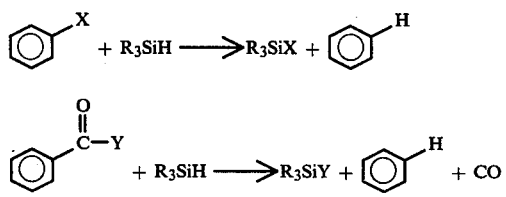

(X is halogen and Y is hydrogen or halogen)
Often over 50% of the silane within the reaction mixture is converted to the silane-complexes $R_3SiY$ and $R_3SiX$. These silane complexes are often useful materials in other processes, such as endcapping or forming siloxane polymers. Other competing reactions include the hydrosilation of aromatic aldehydes to the corresponding aryl silyl-ether.

The following examples are provided to illustrate the invention and are not intended to limit the scope of this invention to the embodiments described.

EXAMPLES I–IV

A stock solution of 22.5 gm (165 mol) of phenyldimethyl silane and 23.2 gm (165 mmol) benzoyl chloride was divided into 4 equal parts and each were heated to about 180° C. for about 16 hours in the presence of 0.1% by weight of various catalysts shown in Table I in a thick walled pyrex tube sealed under vacuum. The percent yield of aryl silane products and by-products obtained with each transition metal complex is illustrated in Table I, which were determined by gas/liquid chromatography.

TABLE I

| | Catalyst | Substrates | % Diphenyl-dimethyl Silane | % Co-product |
|---|---|---|---|---|
| (I) | ClRh(PPh₃)₃ | PhMe₂SiH, Ph(CO)Cl | 12 | 80 |
| (II) | ClRh(CO)(PMe₃)₂ | PhMe₂SiH, Ph(CO)Cl | 10 | 90 |
| (III) | HRh(CO)(PPh₃)₃ | PhMe₂SiH, Ph(CO)Cl | 25 | 70 |
| (IV) | Cl₂Ru(PPh₃)₃ | PhMe₂SiH, Ph(CO)Cl | 8 | 90 |

EXAMPLES V–VIII

Dichloromethylsilane was reacted with 3 different aromatic compounds under the same reaction conditions as Examples I–IV in the presence of various transition metal catalysts (0.1% by weight). The percent yield of desired product, phenyldichloromethylsilane, was determined by GLC analysis. The aromatic compounds and the transition metal catalysts utilized along with the percent yield of desired product obtained are indicated in Table II.

TABLE II

| Silane | Aromatic Compound | Catalyst | % PhCl$_2$MeSi | % Coproduct |
|---|---|---|---|---|
| Cl$_2$MeSiH | Ph(CO)Cl | ClRh(CO)(PPh$_3$)$_2$ | 10 | 90 |
| Cl$_2$MeSiH | Ph(CO)H | ClRh(CO)(PPh$_3$)$_2$ | 18 | 40 |
| Cl$_2$MeSiH | PhBr | Pd(PPh$_3$)$_3$* | 5 | 100 |
| Cl$_2$MeSiH | PhBr | 5% Pd** | 10 | 90 |

*on polystyrene
**on carbon

EXAMPLES IX–XI

The effect of reacting triethylsilane with various aromatic compounds in the presence of various transition metal catalysts is illustrated in these examples. Reaction mixtures containing triethylsilane and various aromatic compounds were placed under the same conditions as the reaction samples of Examples I–IV in the presence of various transition metal catalysts in a quantity of 0.1% by weight. The percent yield of triethylphenyl silane was determined by GLC analysis. The results obtained from the various samples are illustrated in Table III.

TABLE III

| Silane | Aromatic Compound | Catalyst | % PhEt$_3$SiH | % Coproduct |
|---|---|---|---|---|
| Et$_3$SiH | Ph(CO)Cl | Cl$_2$Pd(PPh$_3$)$_2$ | 12 | 90 |
| Et$_3$SiH | PhBr | Cl$_2$Pd(PPh$_3$)$_2$ | 35 | 60 |
| Et$_3$SiH | PhBr | Me$_2$Pt(PEt$_3$)$_2$ | 15 | 80 |

EXAMPLE XII

This example demonstrates the inability of unsubstituted benzene to provide Si-H addition at temperatures of about 180° C. in the presence of transition metal catalysts of the following formulas C$_5$H$_5$Mn(CO)$_3$, C$_3$H$_5$Mn(CO)$_4$, C$_3$H$_5$CO[P(OMe)$_3$]$_3$.

Three reaction mixtures of triethylsilane and benzene were placed under the same reaction conditions as the reaction mixtures of Examples I–IV in that these reaction mixtures were heated to 180° C. for approximately 16 hours. The production of triethylphenyl silane was not observed although each of the following catalysts were added to the three reaction mixtures, respectively: C$_5$H$_5$Mn(CO)$_3$, C$_3$H$_5$Mn(CO)$_4$ and C$_3$H$_5$Co[P(OMe)$_3$]$_3$.

Although the above examples have shown various modifications of the present invention, further modifications are possible by one skilled in the art without departing from the scope and spirit of this invention.

What is claimed is:

1. A method which comprises effecting reaction between a silane having at least one hydrogen-silicon bond and a compound of from 6 to 30 carbon atoms having an aromatic nucleus and at least one monovalent radical selected from the class consisting of halogen and carbonyl groups of the formula $$-\overset{O}{\underset{\|}{C}}-Y,$$

wherein Y is selected from a group consisting of hydrogen and halogen, in the presence of a catalytic quantity of a transition metal at a temperature in the range of about 150° C. to about 200° C.

2. A method which comprises effecting reaction between a silane of the formula

HSiR$_3$ and a compound selected from a group of substituted aromatic compounds having the formulas $$ArX_n \text{ and } Ar-(\overset{O}{\underset{\|}{C}}-Y)_n,$$

wherein R is a monovalent radical selected from the class consisting of hydrogen, halogen and organic radicals of from 1 to 30 carbon atoms, Ar is selected from a group consisting of polyvalent and monovalent aromatic radicals of from 6 to 30 carbon atoms, X is halogen and Y is selected from the group consisting of hydrogen and halogen in the presence of a catalytic quantity of a transition metal at a temperature in the range of about 150° to about 200° C.

3. A method as in claim 2 wherein the transition metal is selected from the group consisting of ruthenium, rhodium, platinum, palladium, osmium and iridium.

4. A method as in claim 3 wherein X and Y are selected from the group consisting of chlorine and bromine.

5. A method of claim 3 wherein R is selected from the group consisting of methyl, ethyl, chloro, bromo and phenyl.

6. A method as in claim 5 wherein the transition metal is utilized as a heterogeneous catalyst by combining said transition metal with an inert substrate.

7. A method as in claim 6 wherein the inert substrate is selected from the group consisting of carbon and polystyrene.

8. A method as in claim 3 wherein the transition metal is in the form of a soluble complex and is utilized as a homogeneous catalyst.

9. A method as in claim 8 wherein the ligands of the transition metal complex are selected from the class consisting of alkyl, aryl, hydride, phosphine and carbonyl groups, amines and halides.

10. A method as in claim 9 wherein the transition metal complex is selected from the group consisting of ClRh(PPh$_3$)$_3$ ClRh(CO)(PMe$_3$)$_2$ ClRh(CO)(PPh$_3$)$_2$ HRh(CO)(PPh$_3$)$_3$ Cl$_2$Pd(PPh$_3$)$_2$ Me$_2$Pt(PEt$_3$)$_2$ and

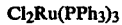

11. A method as in claim 3 wherein the aromatic compound is selected from the group consisting of chlorobenzene and bromobenzene, benzaldehyde, and benzoyl chloride.

12. A method as in claim 3 wherein the silane is selected from a group consisting of triethylsilane, dimethylchlorosilane, phenyldimethylsilane, and dichloromethylsilane.

13. A method of producing triethylphenylsilane by effecting reaction between bromobenzene and triethylsilane in the presence of 0.01 to 1 weight percent of dichlorobis(triphenylphosphine) palladium at a temperature within the range of about 150°–200° C.

14. A method of producing dichloromethylphenylsilane by effecting reaction between bromobenzene and dichloromethylsilane in the presence of 1 to 10% by weight of a catalyst selected from the group consisting of palladium and tris(triphenylphosphine) palladium on a solid carrier at a temperature in the range of about 150°–200° C.

15. A method as in claim 14 wherein the solid carrier is selected from the group consisting of polystryene and carbon.

* * * * *